United States Patent [19]

Fuhr

[11] Patent Number: 5,094,524
[45] Date of Patent: Mar. 10, 1992

[54] METHOD OF VISUAL TESTING AND RELATED PRODUCT

[76] Inventor: Patti W. Fuhr, 719 D Raleigh Ct., Birmingham, Ala. 35209

[21] Appl. No.: 495,325

[22] Filed: Mar. 19, 1990

[51] Int. Cl.$^5$ .............................................. A61B 3/00
[52] U.S. Cl. ..................................... 351/246; 351/203
[58] Field of Search ............... 351/224, 225, 226, 246, 351/203

[56] References Cited

U.S. PATENT DOCUMENTS

| | | |
|---|---|---|
| 2,206,303 | 7/1940 | Neumueller et al. ............... 351/246 |
| 3,092,103 | 11/1959 | Mower . |
| 3,416,857 | 12/1968 | Lookabaugh ..................... 351/246 |
| 3,902,795 | 9/1975 | Owen . |
| 4,682,371 | 7/1987 | Heltman . |
| 4,701,962 | 10/1987 | Simon . |
| 4,709,695 | 12/1987 | Kohn et al. . |
| 4,786,142 | 11/1989 | Karecki . |
| 4,793,003 | 12/1988 | Riedel et al. . |

OTHER PUBLICATIONS

S. J. Bolanowski, Jr. and R. W. Doty; Perceptual "Blankout" of Monocular Homogeneous Fields (Ganzfelder) is Prevented with Binocular Viewing; Vision Res. vol. 27, No. 6, pp. 967-982, 1987.

H. Goldmann; Lichtsinn mit besonder Beruchksictigung der Perimetrie; Schweiz, Ophthal. Ges., 2, Fortbildungskurs, Bern 1968; Opthalmologica 158: 362-386 (1969).

Primary Examiner—Paul M. Dzierzynski
Attorney, Agent, or Firm—Bell, Seltzer, Park & Gibson

[57] ABSTRACT

A method of increasing the reliability of visual field testing by preventing intermittent darkening of the visual field during visual field analysis and that is particularly useful in applications of bowl perimetry comprises occluding one eye of a subject, measuring the visual field perception of the unoccluded eye of the subject, while providing sufficient illumination to the occluded eye to eliminate intermittent darkening of the visual field perceived by the unoccluded eye, and while reducing visual acuity in the occluded eye to a level that prevents interference with the visual field testing of the unoccluded eye.

21 Claims, 3 Drawing Sheets

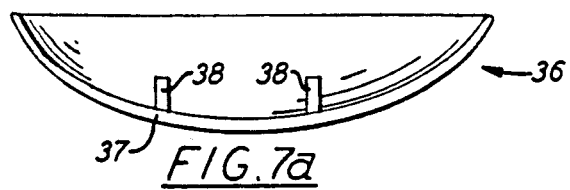
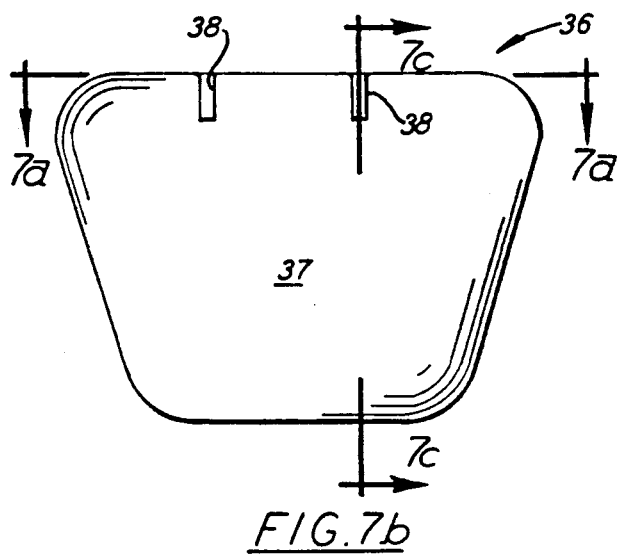
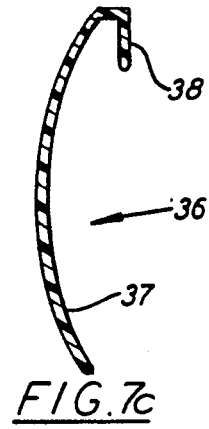
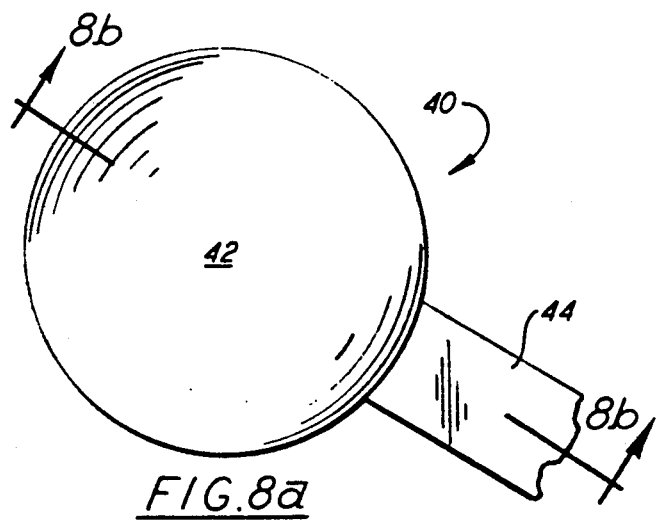
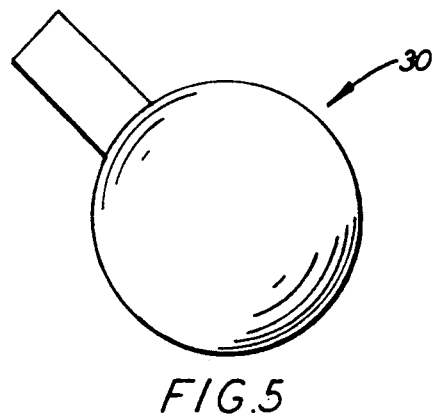
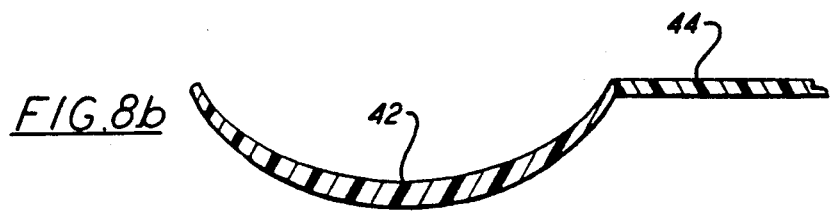

METHOD OF VISUAL TESTING AND RELATED PRODUCT

FIELD OF THE INVENTION

The present invention relates to visual field testing and in particular relates to a method of increasing the reliability of visual field testing by preventing intermittent darkening of the visual field during visual field analysis, particularly during bowl perimetry.

BACKGROUND

Visual field testing also referred to as "visual field analysis" is a fundamental and important part of both routine and specialized eye examinations. According to historians in this art, visual field defects have been noted for centuries beginning perhaps as early as Hippocrates (circa 460-380 B.C.), and the techniques, observations and interpretations of visual field analysis have continued throughout medical history. For at least the last century, it has been well understood that the visual field is as important a measurement of a patient's visual function as is central visual acuity. As understood by those of ordinary skill in this art, the normal visual field of an eye is a slightly irregular oval. From its center, it extends approximately 50° in the superior direction (towards the eyebrow), about 70° in the inferior direction (towards the feet), about 90°-100° temporally (toward the ear), and about 60° nasally (toward the nose). When the visual field of a patient differs substantially from these norms, particularly in a decreasing fashion, some associated medical problem is most likely indicated. Problems that are exhibited by a change in the visual field include glaucoma, neurologic problems such as lesions of the chiasm, optic tract defects, temporal lobe lesions, parietal lobe lesions, occipital lobe lesions, toxic amblyopias, and other non-neurological diseases including various diseases of the retina, choroid and media. Visual field analysis is also an important test in the diagnosis and management of other diseases including diabetes, brain tumors, and cerebro-vascular accidents.

The visual field of a patient can be tested in various manners, but as suggested by the nature of the visual field, these techniques generally comprise methods of measuring the points at which a patient's eye can discriminate certain sensory input such as flashes of light within the visual field. Basically, a patient's visual field is analyzed by moving a test spot such as an object or point of light from an area of non-vision to an area of vision (kinetic techniques) or by increasing the test spot intensity until it can be seen at a fixed location (static techniques).

Typical testing methods include "confrontations" in which a patient is asked to detect the examiner's fingers in different quadrants of vision at a distance of about 1 meter; tangent screen, in which the patient is usually seated at a distance of about 1 meter from a black screen while a target of varying dimensions is manually moved through the different quadrants of vision; and bow perimetry. In bowl perimetry, the patient is seated with his head positioned on a chin rest with the head extending into a lighted hemisphere. One eye is covered and the patient is required to fixate on a stationary or moving target and to signal when he detects a light flash (stationary testing) or movement into or out of (moving target) the visual field.

Because of the nature of human vision in which the eyes work together and are coordinated by the brain to produce the images perceived by the subject, and because the visual fields of each eye overlap, the task of measuring the visual field of one eye requires that the other eye be covered or occluded during the testing procedure. The untested eye is thus generally covered with an opaque device such as an eye patch in order to prevent as much light as possible from entering the covered eye and interfering with the test.

Recently, S. J. Bolanowski and R. J. Doty have reported in perceptual "*Blankout*" *of Monocular Homogenous Fields (Ganzfelder) Is Prevented With Binocular Viewing*, Vision Res. Vol. 27, No. 6, pp. 967-982, 1987, that when one eye is presented with darkness and the other is presented with a homogenous light field (a "Ganzfeld"), a loss of visual perception in the form of an intermittent darkening or "blankout" occurs in the eye presented with the light field. The blankout phenomenon has been reported as "a dramatic vanishing of visual sensation despite continuing simulation." This blankout is so persistent that it has been used to test the sufficiency of adequate Ganzfeld illumination and retinal stabilization. Bolanowski and Doty were able to determine that such Ganzfeld blankout could be minimized or eliminated if a sufficient amount of illumination was provided to each eye. They did not, however, perform any visual field testing, did not occlude either eye, and did not test visual acuity. Moreover, a Ganzfeld provides no clues to depth or depth accommodation, and Bolanowski's and Doty's experiment gave no indication that the blankout phenomena would occur during visual testing in general or visual field testing in particular.

Therefore, prior to the present invention, the phenomena of blankout or its cure had not been addressed with respect to the important technique of visual field testing. As described further herein with respect to the present invention, it has now been discovered that blankout occurs during visual field testing. Because of the diagnostic importance of visual field testing, there exists the need for procedures and devices that can minimize or eliminate the blankout phenomena during such testing.

OBJECT AND SUMMARY OF THE INVENTION

It is accordingly an object of the present invention to increase the reliability of visual field testing by preventing such intermittent darkening or blankout of the visual field. The invention meets this and other objects by a method which comprises occluding one eye of a subject, measuring the visual field perception of the unoccluded eye of the subject, while providing sufficient illumination to the occluded eye to eliminate intermittent darkening of the visual field perceived by the unoccluded eye, and while reducing visual acuity in the occluded eye to a level that prevents interference with the visual field testing of the unoccluded eye.

The foregoing and other objects, advantages and features of the invention, and the manner in which the same are accomplished, will become more readily apparent upon consideration of the following detailed description of the invention taken in conjunction with the accompanying drawings, which illustrate preferred and exemplary embodiments, and wherein:

FIG. 5 is an occluder in the form of a trial lens;

FIGS. 7a, 7b and 7c are corresponding views of a second embodiment of an occluder for use with eyeglasses or spectacle frames; and FIGS. 8a and 8b are respective partial elevational and partial cross-sectional views of a hand held occluder according to the present invention.

DETAILED DESCRIPTION OF THE PREFERRED EMBODIMENTS

Figure 1A:
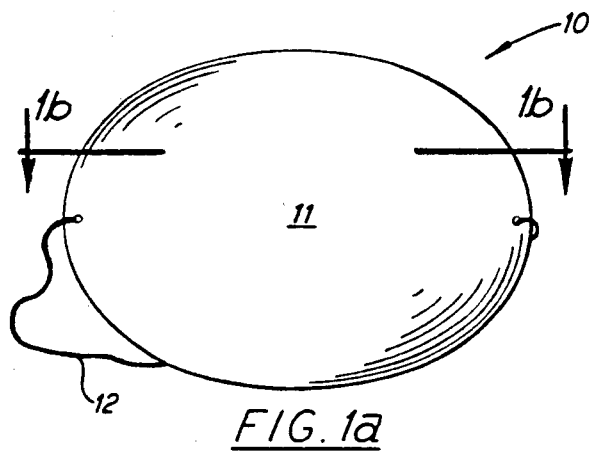
FIGS. 1a and 1b are respective elevational and cross-sectional views of an occluder for practicing the method of the present invention.

In order to identify and solve the problem of blankout during bowl perimetry visual field testing, ten normal subjects underwent visual field testing in a controlled test. These subjects met appropriate criteria of age, visual acuity, stereo vision, generally normal ocular health, and normal visual fields.

In a first experiment, the objective was to determine whether the individuals experienced intermittent darkening of the visual field in a visual field analyzer and to determine under what conditions the intermittent darkening occurred. Accordingly, the subjects were tested under three conditions, binocularly, with one eye occluded with a standard black opaque patch, and with the non-tested eye occluded with a translucent patch.

Each subject was tested in a Humphrey Visual Field Analyzer and viewed a central fixation target for two minutes under each of the three conditions. None of the subjects noted any darkening of the visual field while viewing the bowl binocularly. When the non-viewing eye was occluded with an opaque patch, eight of the ten described an intermittent darkening of the visual field. Using the translucent patch, none of the subjects noted any apparent darkening of the visual field.

In related experiments, the subjects were tested to quantify the blankout phenomenon; to determine whether the sensitivity and variability of the phenomenon was the same using a translucent patch and an opaque patch; and to determine whether a difference in visual comfort existed between an opaque patch and a translucent patch during their use in automated bowl perimetry.

Based upon these experiments, the subjects described changing perceptions of the visual field which were perceived as dark or light. These experiments also established that even though a field analyzer is not a Ganzfeld, an intermittent darkening does occur during visual field testing. This phenomenon has not been previously reported to have occurred during visual field testing.

Therefore, in order to address the problem, it has now been determined according to the present invention that the reliability of visual field testing can be increased by preventing intermittent darkening of the visual field, particularly during bowl perimetry, by a method of testing which comprises occluding one eye of a subject, measuring the visual field perception of the unoccluded eye of the subject, while providing sufficient illumination to the occluded eye to eliminate intermittent darkening of the visual field perceived by the unoccluded eye, and while reducing visual acuity in the occluded eye to a level that prevents interference with the visual field perception of the unoccluded eye. In particular, the step of providing sufficient illumination to the occluded eye preferably comprises providing an illumination intensity to the occluded eye that is at least about 0.50 log units of intensity of the illumination intensity provided to the unoccluded eye. As known to those familiar with this art, illumination intensities for visual field testing fall within certain ranges. These ranges are rather broad and cover several orders of magnitude, so that log units are commonly used to compare or describe illumination intensities.

Stated differently, the method of increasing the sensitivity of the tested eye comprises providing sufficient illumination to the occluded or untested eye that is at least about 30 percent of the illumination intensity provided to the unoccluded eye, and most preferably comprises providing an illumination intensity to the occluded eye that is about 40 percent of the illumination intensity provided to the unoccluded eye.

Furthermore, because visual acuity to the occluded eye must be reduced while still providing the additional illumination, it has been determined according to the present invention that visual acuity should preferably be reduced to a point that prevents form vision in the occluded eye. An acuity that has been reduced to hand motion at a distance of about twelve centimeters or less has been found to be satisfactory (i.e. at this acuity even such hand motion cannot be observed beyond 12 centimeters). In a visual field testing device, the visual acuity should be reduced to a point that prevents the occluded eye from seeing the target.

As presently best understood, a relative illumination to the occluded eye that is about 30 percent (or about 0.50 log units) of that provided to the tested eye is a satisfactory minimum level of illumination to accomplish the invention. Presently, there does not appear to be any upper limit of illumination, provided that visual acuity—which is generally enhanced by greater illumination—remains minimal at such higher illuminations. Using the materials for occluders that are discussed in further detail later herein, however, a range of illumination to the occluded eye of between about 30 and 60 percent (0.5 to 0.75 log units) of that provided to the unoccluded eye has been found to be satisfactory.

It has been further discovered according to the present invention that the preferred method of increasing the reliability of visual field testing can comprise measuring the visual field perception of an unoccluded eye of a subject while covering the other eye with an occluder that sufficiently reduces visual acuity to a level that prevents interference with the visual field testing of the unoccluded eye, but that transmits sufficient light intensity to the occluded eye to prevent intermittent darkening of the visual field perceived by the unoccluded eye.

More specifically, the method can comprise the step of covering the other eye with an occluder that has a modulation transfer function (MTF) that is substantially or effectively zero. As understood by those familiar with this art, the modulation transfer function of a lens or any other object is a measure of the amount of visual information that the lens or object will transmit. Modulation transfer function can be expressed in lines per centimeter of visual resolution, and a good camera lens will have a modulation function of up to 400 lines per centimeter, while the human eye can perceive at a resolution of about 40 lines per centimeter. Thus, the modulation transfer function is one measure of whether an occluder used in accordance with the present invention is satisfactory. It will be understood that although an ideal modulation transfer function for use with the invention would be zero, other low modulation transfer functions are appropriate, provided they do not interfere with the testing of the nonoccluded eye.

Stated alternatively, the step of covering the other eye with an occluder can comprise covering the eye with an occluder that provides the occluded eye with between about 30 and 60 percent of the illumination intensity provided to the unoccluded eye. Thus, an acceptable occluder will transmit between about 30 and 60 percent of the illumination intensity incident upon it. Because illumination intensity is often measured, compared and expressed in logarithmic units of intensity, the invention also comprises covering the other eye with an occluder that reduces the illumination intensity to the occluded eye to an intensity that is between about 0.50 and 0.75 log units of intensity of the illumination intensity provided the unoccluded eye.

Such a ratio, is of course, a relative measurement. Nevertheless, it is well understood by those familiar with visual field testing that the brightest targets on typical visual field analyzers have an intensity of approximately 10,000 apostilbs (asb), and that the relationship between apostilbs and candles per square meter ($cd/m^2$) is such that 1 $cd/m^2$ = 3.15 asb. Additionally, the background illumination of typical bowl perimeter analyzers is about 4 to 10 candles per square meter. Thus, the range of target illumination intensity provided by such analyzers (about 1 to 10,000 asb) represents a range of about 4 log units of intensity, so that the difference in absolute intensity required to produce the desired relative intensity can be easily calculated.

For example, if about 10 $cd/m^2$ of background illumination is provided to the tested eye, at least about 3 $cd/m^2$ of background illuminates should be provided to the occluded eye. Calculated logarithmically, 10 $cd/m^2$ has a log intensity of 1.0. A minimum illumination to the occluded eye should therefore be within about 0.5 log units, or 0.5. A log intensity of 0.5 represents an absolute illumination of about 3.16 $cd/m^2$ (i.e. between about 31 and 32 percent).

Based upon these relationships, the invention further comprises an occluder for increasing the reliability of visual field testing and which comprises means for reducing visual acuity in an occluded eye to a level that prevents interference with the visual field testing of the unoccluded eye, and means for providing sufficient illumination to the occluded eye to eliminate intermittent darkening of the visual field perceived by the unoccluded eye. In preferred embodiments, the occluder comprises an eye covering which provides an illumination intensity to the occluded eye that is between 30 and 60 percent of the illumination intensity provided to the unoccluded eye. As stated earlier, this can also be expressed as an eye covering that provides a illumination intensity to the occluded eye that is between about 0.50 and 0.75 log units of intensity of the illumination intensity provided to the unoccluded eye.

As also stated earlier, an important factor in the method of the invention is that visual acuity must also be reduced in order to practice the successful method of the invention. Visual acuity is often defined as the relative ability of the eye to resolve detail, and expressed as either the reciprocal of the minimum angular separation of two lines just resolvable as separate, or as lines resolvable per centimeter. Therefore, a preferred occluder will comprise an eye covering that reduces visual acuity in the occluded eye to hand motion at a distance of about 12 centimeters or less. Expressed differently, the occluder can comprise a covering or lens with a modulation transfer function of zero. As is understood by those in this art, the distance at which most visual testing takes place is normally no closer than about 33 centimeters from the cornea for adults, and about 20 centimeters for children. At these distances, the modulation transfer function of the preferred occluder is zero, therefore there is no usable vision in the occluded eye and no interference with the testing of the nonoccluded eye.

Figure 1B:
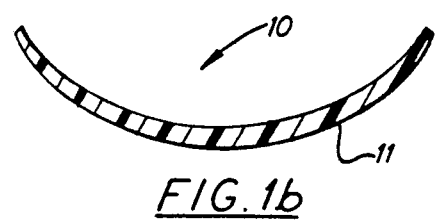

The drawings show various embodiments of an occluder according to the present invention. FIGS. 1a and 1b show an occluder broadly designated at 10 in the form of an eye patch 11 and carrying a simple elastic band 12 for holding the patch 10 across the occluded eye of a patient. In preferred embodiments, the patch is formed of a translucent polyethylene which has been found to be most satisfactory in providing the combination of illumination intensity and reduction in visual acuity in accordance with the present invention. The appropriate molecular weight, degree of orientation and the like of the polyethylene that has such properties can be determined by those familiar with such materials without undue experimentation. As illustrated in FIGS. 1a and 1b, a typical patch has an elliptical shape and is on the order of about 70 millimeters on its long axis and 50 millimeters on the short axis. The patch 10 will be between about 0.5 and 3 millimeters in thickness and will be positioned so that there is about 15 millimeters of space between the cornea and the generally centermost portion of the patch.

Figure 2A:
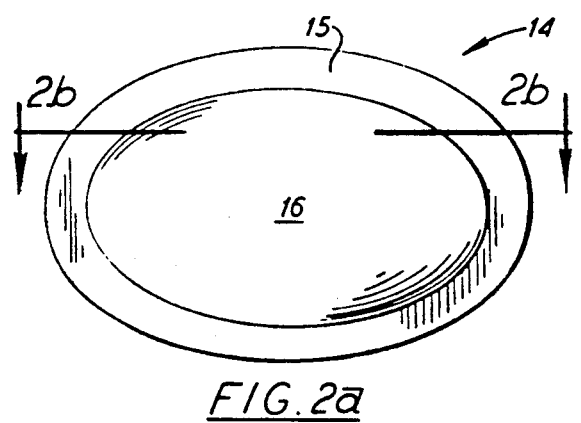
FIGS. 2a and 2b are similar views of a second embodiment of such an occluder.
Figure 2B:
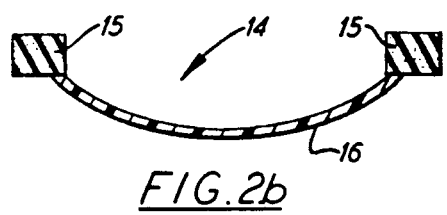

FIGS. 2a and 2b show a second embodiment broadly designated at 14 in which a foam rim 15 is provided to cushion a patch 16 against the eye of a patient. The occluder 14 illustrated in FIGS. 2a and 2b can likewise be held in place by a simple elastic band (not shown) similar to the band 12 illustrated in FIG. 1a.

Figure 3A:
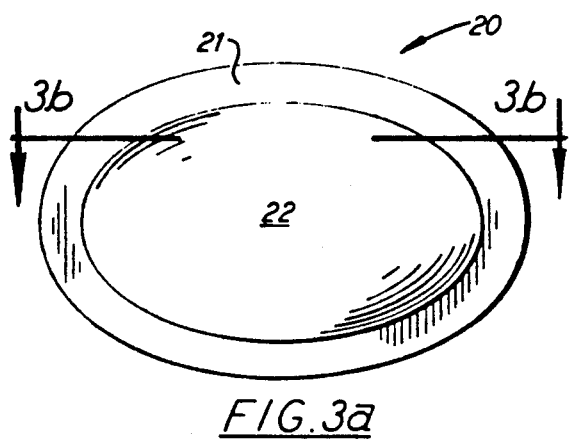
FIGS. 3a and 3b are similar views of a third embodiment of a such an occluder.
Figure 3B:
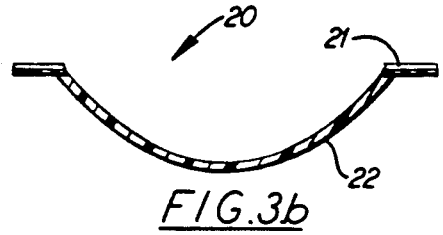

FIGS. 3a and 3b illustrate a third embodiment broadly designated at 20 of an occluder according to the present invention which includes adhesive tape 21 for holding a patch 22 against the eye of a patient.

Figure 4A:
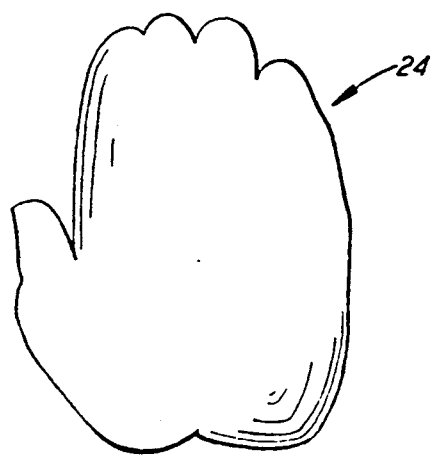
FIGS. 4a, 4b and 4c are occluders formed in various fanciful shapes potentially attractive to children.
Figure 4B:
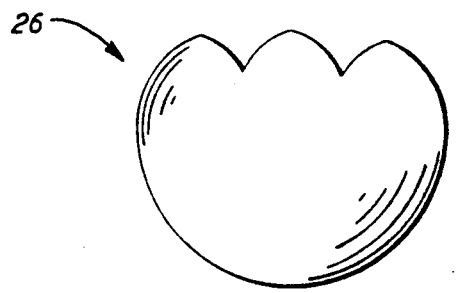
Figure 4C:
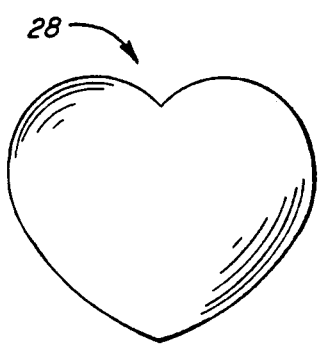

FIGS. 4a, 4b and 4c show fanciful designs for the respective occluders 24, 26, and 28 which would be useful with subjects such as children who would be entertained by the fanciful designs and will thereby cooperate more easily in the testing procedure.

FIG. 5 shows an occluder 30 in the form of the common trial lens which can be quickly added to or removed from common optical testing devices.

Figure 6A:
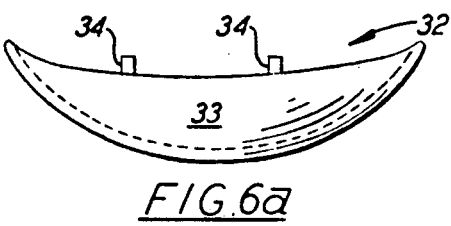
FIGS. 6a, 6b and 6c are top plan, side elevational and cross-sectional views respectively of an occluder according to the present invention which can be used in conjunction with spectacle frames.
Figure 6B:
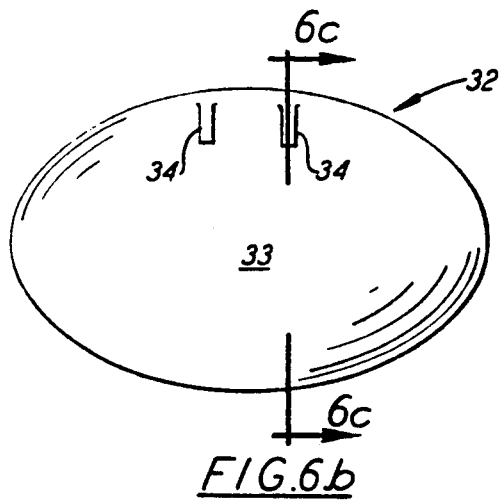
Figure 6C:
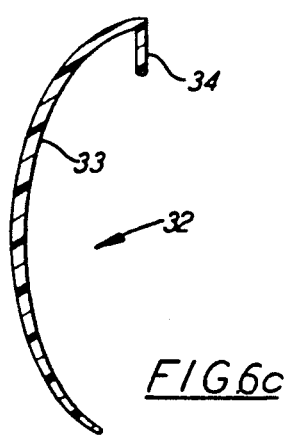

FIGS. 6a, 6b and 6c show an occluder 32 according to the present invention which further comprises means shown as the small overlapping hooks 34 for attaching the covering 33 to a pair of spectacle frames or eye glasses where such are required to be worn by the patient during the test procedure.

FIGS. 7a, 7b and 7c show a similar occluder 36 formed of a patch 37 with similar hooks 38 for the identical purpose as the occluder shown in FIGS. 6a, 6b and 6c, but in a slightly different shape as may be required depending upon the shape of the eye glasses or spectacle frames worn by the patient.

Finally FIGS. 8a and 8b show a hand held occluder 40 according to the present invention which includes a eye covering 42 and a handle 44.

All of these embodiments can be formed of a number of materials including various polymers such as the polyethylene already discussed, other thermoplastic or thermosetting materials, glass, or even appropriate forms of paper or other fibrous materials such as nonwoven, woven or knitted textile products. The surface can be smooth or stippled and the device is preferably shatterproof. Those familiar with materials such as polyethylene can conveniently manufacture it in forms suitable for the invention.

It has been found to the according to the present invention, however, that the occluder is most preferably made of a material which is easily and safely disposed of and which has a moderate or low cost so that the occluder can be used once with a single patient and then disposed of following the testing of the eye or eyes. The nature of the physiology of the eye, particularly its characteristic as a mucous membrane and fluid containing organ exposed to ambient surroundings, makes the eye a particularly sensitive entry point for microorganisms or other easily transmitted materials. Thus, the eye is a convenient entry point for the common cold virus, but more importantly may also be a convenient entry point under some circumstances for more serious diseases such as acquired immune deficiency syndrome (AIDS) that can be transmitted through fluid contact. The preferred embodiment of the occluder therefore is formed of an appropriate material such as polyethylene which can be used with one patient and then discarded. The use of a disposable occluder likewise enhances the hygienic standards in the practitioner's office where the occluder is used.

As illustrated in the drawings, the oval shape of the various occluders and the use of foam or tape allows more complete apposition to the facial structures of a patient to thereby prevent gaps between the occluder and the face which could cause errors or artifacts in visual testing. The generally hemispherical shape of the device allows the eye to remain open with the eyelashes of the patient free of apposition to the surface of the occluder.

Finally, in accordance with the present invention, it is hypothesized that the key to the invention may be the reduction in visual acuity that is combined with the difference in illumination as well as the difference in illumination intensity itself. Therefore, it is expected that the illumination intensity levels to both the occluded and the nonoccluded eye can be very similar provided that the visual acuity to the occluded eye is appropriately reduced. In other words, the occluded eye could be back illuminated to a level equivalent to the nonoccluded eye so long as the modulation transfer function presented to the occluded eye remains extremely low or zero. Stated differently, the back illumination would have to be diffuse enough for the occluded eye to be unable to see the visual field targets that the unoccluded eye could see.

It will be further understood to those familiar with this art that although translucent patches have previously been used to prevent dark adaptation, such adaptation is a totally different phenomena than the intermittent darkening to which the present invention is addressed. Likewise, commonly available conventional patches generally transmit far too little light to be of any use in the present invention.

The invention resultingly increases the sensitivity of the nonoccluded eye during visual field testing, decreases retest threshold variability in the nonoccluded eye, and increases patient comfort. All of these factors result in an increased reliability in such testing.

It is likewise expected that the invention will be useful for occlusion therapy of amblyopic children and for other related vision training procedures.

In the drawings and specification, there have been disclosed typical preferred embodiments of the invention and, although specific terms have been employed, they have been used in a generic and descriptive sense only and not for purposes of limitation, the scope of the invention being set forth in the following claims.

That which is claimed is:

1. A method of increasing the reliability of visual field testing by preventing intermittent darkening of the visual field during visual field analysis, and that is particularly useful in applications of bowl perimetry, the method comprising:

occluding one eye of a subject;

measuring the visual field perception of the unoccluded eye of the subject; while providing an illumination intensity to the occluded eye that is at least about 30 percent of the illumination intensity provided to the unoccluded eye to thereby eliminate intermittent darkening of the visual field perceived by the unoccluded eye; and while reducing visual acuity in the occluded eye to a level that prevents interference with the visual field testing of the unoccluded eye.

2. A method according to claim 1 wherein the step of reducing visual acuity comprises substantially preventing form vision in the occluded eye.

3. A method according to claim 1 wherein the step of providing an illumination intensity to the occluded eye comprises providing an illumination intensity to the occluded eye that is at least about 0.50 log units of intensity of the illumination intensity provided to the unoccluded eye.

4. A method according to claim 1 wherein the step of eliminating any interfering visual acuity in the occluded eye comprises reducing visual acuity in the occluded eye to hand motion at a distance of about 12 centimeters or less.

5. A method according to claim 1 wherein the step of measuring the visual field perception of the unoccluded eye of the subject comprises measuring the visual field perception using bowl perimetry.

6. A method of increasing the reliability of visual field testing by preventing intermittent darkening of the visual field during visual field analysis, and that is particularly useful in applications of bowl perimetry, the method comprising:

measuring the visual field perception of an unoccluded eye of a subject; while covering the other eye with an occluder that provides the occluded eye with between about 30 and 60 percent of the illumination intensity provided to the unoccluded eye and prevents interference with the visual field testing of the unoccluded eye, but that transmits a sufficient amount of incident light to provide a light intensity to the occluded eye that prevents intermittent darkening of the visual field of the unoccluded eye.

7. A method according to claim 6 wherein the step of covering the other eye with an occluder comprises covering the eye with an occluder that has a modulation transfer function that is effectively zero.

8. A method according to claim 6 wherein the step of covering the other eye with an occluder comprises covering the other eye with an occluder that transmits an illumination intensity that is at least about 0.50 log units of intensity of the illumination intensity incident thereon.

9. A method according to claim 6 further comprising disposing of the occluder following the step of measuring the visual field perception of the unoccluded eye of the subject.

10. A method of increasing the sensitivity of the eye to visual field testing while increasing the reliability of the testing by preventing intermittent darkening of the visual field during visual field analysis, the method comprising:
    positioning the head of a subject in proper relationship to a bowl perimeter visual field analyzer;
    occluding one eye of the subject;
    measuring the visual field perception of the unoccluded eye of the subject in the bowl perimeter analyzer; while
    providing an illumination intensity to the occluded eye that is at least about 30 percent of the illumination intensity provided to the unoccluded eye to thereby eliminate intermittent darkening of the visual field perceived by the unoccluded eye; and while
    reducing visual acuity in the occluded eye to a level that prevents interference with the visual field testing of the unoccluded eye.

11. An occluder for increasing the reliability of visual field testing by preventing intermittent darkening of the visual field during visual field analysis and that is particularly useful in applications of bowl perimetry, said occluder comprising an eye covering that reduces visual acuity in an occluded eye to a level that prevents interference with the visual field testing of the unoccluded eye while transmitting an illumination intensity that is between about 30 and 60 percent of the illumination intensity incident thereon to provide the occluded eye with sufficient illumination to eliminate intermittent darkening of the visual field perceived by the unoccluded eye.

12. An occluder according to claim 11 wherein said eye covering transmits an illumination intensity that is between about 0.50 and 0.75 log units of intensity of the illumination intensity incident thereon.

13. An occluder according to claim 11 wherein said eye covering reduces visual acuity in the occluded eye to hand motion at a distance of about 12 centimeters or less.

14. An occluder according to claim 11 wherein said eye covering comprises a lens with a modulation transfer function that is effectively zero.

15. An occluder according to claim 11 wherein said eye covering is formed of polyethylene.

16. An occluder according to claim 11 wherein said eye covering is formed of paper.

17. An occluder according to claim 11 wherein said eye covering is formed of glass.

18. An occluder according to claim 11 wherein said eye covering comprises an eye patch.

19. An occluder according to claim 11 wherein said eye covering comprises a trial lens.

20. An occluder according to claim 11 wherein said eye covering includes means for suspending the covering from spectacle frames.

21. An occluder according to claim 11 wherein said eye covering includes a handle for forming a hand held occluder with said covering.

* * * * *

UNITED STATES PATENT AND TRADEMARK OFFICE
CERTIFICATE OF CORRECTION

PATENT NO. : 5,094,524
DATED : March 10, 1992
INVENTOR(S) : Patti W. Fuhr

It is certified that error appears in the above-identified patent and that said Letters Patent is hereby corrected as shown below:

On the Title page, item [56],
UNDER "OTHER PUBLICATIONS":

In the last reference, "Beruchksictigung" should be -- Berucksichtigung --.

At column 5, line 24, "ratio, is" should be -- ratio is, --.

At column 7, line 14, delete "to the."

At column 8, line 43, delete "eliminating any interfering" and insert therefor -- reducing --.

At column 8, line 57, "a" should be -- the --.

Signed and Sealed this

Seventeenth Day of August, 1993

Attest:

BRUCE LEHMAN

Attesting Officer

Commissioner of Patents and Trademarks